US008865220B2

(12) United States Patent
Ho et al.

(10) Patent No.: US 8,865,220 B2
(45) Date of Patent: Oct. 21, 2014

(54) METHOD FOR CONTROLLED RELEASE OF PARATHYROID HORMONE FROM ENCAPSULATED POLY(LACTIC-GLYCOLIC)ACID MICROSPHERES

(75) Inventors: Mei-Ling Ho, Kaohsiung (TW); Gwo-Jaw Wang, Taipei (TW); Je-Ken Chang, Kaohsiung (TW); Yin-Chih Fu, Kaohsiung (TW); Cherng-Chyi Tzeng, Kaohsiung (TW); Eswaramoorthy Rajalakshmanan, Kaohsiung (TW)

(73) Assignee: Kaohsiung Medical University, Kaohsiung (TW)

( * ) Notice: Subject to any disclaimer, the term of this patent is extended or adjusted under 35 U.S.C. 154(b) by 317 days.

(21) Appl. No.: 12/814,955

(22) Filed: Jun. 14, 2010

(65) Prior Publication Data

US 2011/0305766 A1    Dec. 15, 2011

(51) Int. Cl.
*A61K 9/16* (2006.01)
*A61K 9/50* (2006.01)
*A61K 38/29* (2006.01)

(52) U.S. Cl.
CPC ............... *A61K 38/29* (2013.01); *A61K 9/5031* (2013.01); *A61K 9/1647* (2013.01)
USPC ........................................................ 424/497

(58) Field of Classification Search
None
See application file for complete search history.

(56) References Cited

U.S. PATENT DOCUMENTS

| | | | | |
|---|---|---|---|---|
| 6,306,406 | B1 * | 10/2001 | Deluca | 424/400 |
| 6,312,708 | B1 * | 11/2001 | Donovan | 424/423 |
| 6,506,399 | B2 * | 1/2003 | Donovan | 424/423 |
| 6,573,238 | B2 * | 6/2003 | Shirley et al. | 424/497 |
| 6,590,081 | B1 | 7/2003 | Zhang | |
| 6,703,037 | B1 * | 3/2004 | Hubbell et al. | 424/426 |
| 7,501,134 | B2 * | 3/2009 | O'Hagan et al. | 424/489 |
| 2003/0026844 | A1 * | 2/2003 | Lee et al. | 424/501 |
| 2003/0125252 | A1 * | 7/2003 | Underhill et al. | 514/12 |
| 2004/0115254 | A1 * | 6/2004 | Niedzinski et al. | 424/450 |
| 2006/0003009 | A1 * | 1/2006 | Rowe et al. | 424/486 |
| 2006/0073207 | A1 * | 4/2006 | Masters et al. | 424/488 |
| 2007/0020295 | A1 * | 1/2007 | Donovan | 424/239.1 |
| 2008/0095849 | A1 * | 4/2008 | Wu et al. | 424/486 |
| 2008/0268063 | A1 * | 10/2008 | Jon et al. | 424/491 |
| 2009/0269414 | A1 * | 10/2009 | Lee et al. | 424/501 |

FOREIGN PATENT DOCUMENTS

EP    1808438 A2 *  7/2007

OTHER PUBLICATIONS

Brewer et al. Human Parathyroid hormone: Amino acid sequence of the amino-terminal residues 1-34. Proc. NAt. Acad. Sci. USA (1972) 69(12):3585-3588.*

Wei et al. The release profiles and bioactivity of parathyroid hormone from poly(lactic-co-glycolic acid) microspheres. Biomaterials 25 (2004) 345-352.*
Henry T. Keutmann et al., Complete Amino Acid Sequence of Human Parathyroid Hormone, Biochemistry, 1978, p. 5723, vol. 17, No. 26.
R. Podbesek et al., Effects of Two treatment Regimes with Synthetic Human Parathyroid Hormone Fragment on Bone Formation and the Tissue Balance of Trabecular Bone in Greyhounds, Endocrinology, 1983, pp. 1000-1006, vol. 112, No. 3, USA.
Robert M. Neer et al, Effect of Parathyroid Hormone (1-34) on Fractures and Bone Mineral Density in Postmenopausal Women with Osteoporosis, The New England Journal of Medicine, May 10, 2001, pp. 1434-1441, vol. 344, No. 19.
Andrea Leone-Bay et al., Oral Delivery of Biologically Active Parathyroid Hormone, Pharmaceutical Research, 2001, pp. 964-970, vol. 18, No. 7.
Valerie Codrons et al., Systemic Delivery of Parathyroid Hormone (1-34) Using Inhalation Dry Powders in Rats, Journal of Pharmaceutical Sciences, May 2003, pp. 938-950, vol. 92, No. 5.
Yasuyuki Suzuki et al., Prevention of Bone Loss in Ovariectomized Rats by Pulsatile Transdermal Iontophoretic Administration of Human PTH(1-34), Journal of Pharmaceutical Sciences, Feb. 2002, pp. 350-361, vol. 91, No. 2.
Jeffrey Bonadio et al., Localized, Direct Plasmid Gene Delivery in vivo: Prolonged Therapy Results in Reproducible Tissue Regeneration, Nature Medicine, Jul. 1999, pp. 753-759, vol. 5, No. 7.
Je-Ken Chang et al., Parathyroid Hormone 1-34 Inhibits Terminal Differentiation of Human Articular Chondrocytes and Osteoarthritis Progression in Rats, Arthritis and Rheumatism, Oct. 2009, pp. 3049-3060, vol. 60, No. 10.
Joseph A. Fix, Oral Controlled Release Technology for Peptides: Status and Future Prospects, Pharmaceutical Research, 1996, pp. 1760-1764, vol. 13, No. 12.
Lichun Lu et al., Controlled Release of Transforming Growth Factor B1 from Biodegradable Polymer Microparticles, Journal of Biomedical Science, 2000, pp. 440-451, vol. 50.
N. Butoescu et al., Intra-Articular Drug Delivery Systems for the Treatment of Rheumatic Diseases: A Review of the Factors Influencing their Performance, European Journal of Pharmaceutics and Biopharmaceutics, 2009, pp. 205-218, vol. 73.
Liggins, R.T. et al., Intra-articular treatment of arthritis with microsphere formulations of paclitaxel: biocompatibility and efficacy determinations in rabbits, Inflamm. res., 2004, 363-372, vol. 53.
Vera B. Morhenn MD et al., Phagocytosis of Different Particulate Dermal Filler Substances by Human Macrophages and Skin Cells, Dermatol Surg, 2002, 484-490, 28, Published by Blackwell Publishing, Inc.
Eijiro Horisawa et al., Size-Dependency of DL-Lactide/Glycolide Copolymer Particulates for Intra-Articular Delivery System on Phagocytosis in Rat Synovium, Pharmaceutical Research, Feb. 2002, 132-139, vol. 19, No. 2.

* cited by examiner

*Primary Examiner* — Robert A Wax
*Assistant Examiner* — Olga V Tcherkasskaya
(74) *Attorney, Agent, or Firm* — WPAT, P.C.; Anthony King

(57) ABSTRACT

The present invention provides a method for producing a controlled release microsphere with mean average size greater than 50 μm, comprising preparing a water-in-oil (w/o) emulsion comprising an inner aqueous layer containing a pharmaceutically effective amount of a biologically active polypeptide with activity similar to parathyroid hormone, and an oil layer containing a polymer substance of poly(lactic-co-glycolic acid) (PLGA), then adding the w/o emulsion into aqueous polyvinyl alcohol (PVA) solution to form a water-in-oil-in-water (w/o/w) double emulsion and then desorbing the solvent in the oil layer. The present invention also provides a controlled release microsphere prepared by the method and use thereof.

8 Claims, 13 Drawing Sheets

(9 of 13 Drawing Sheet(s) Filed in Color)

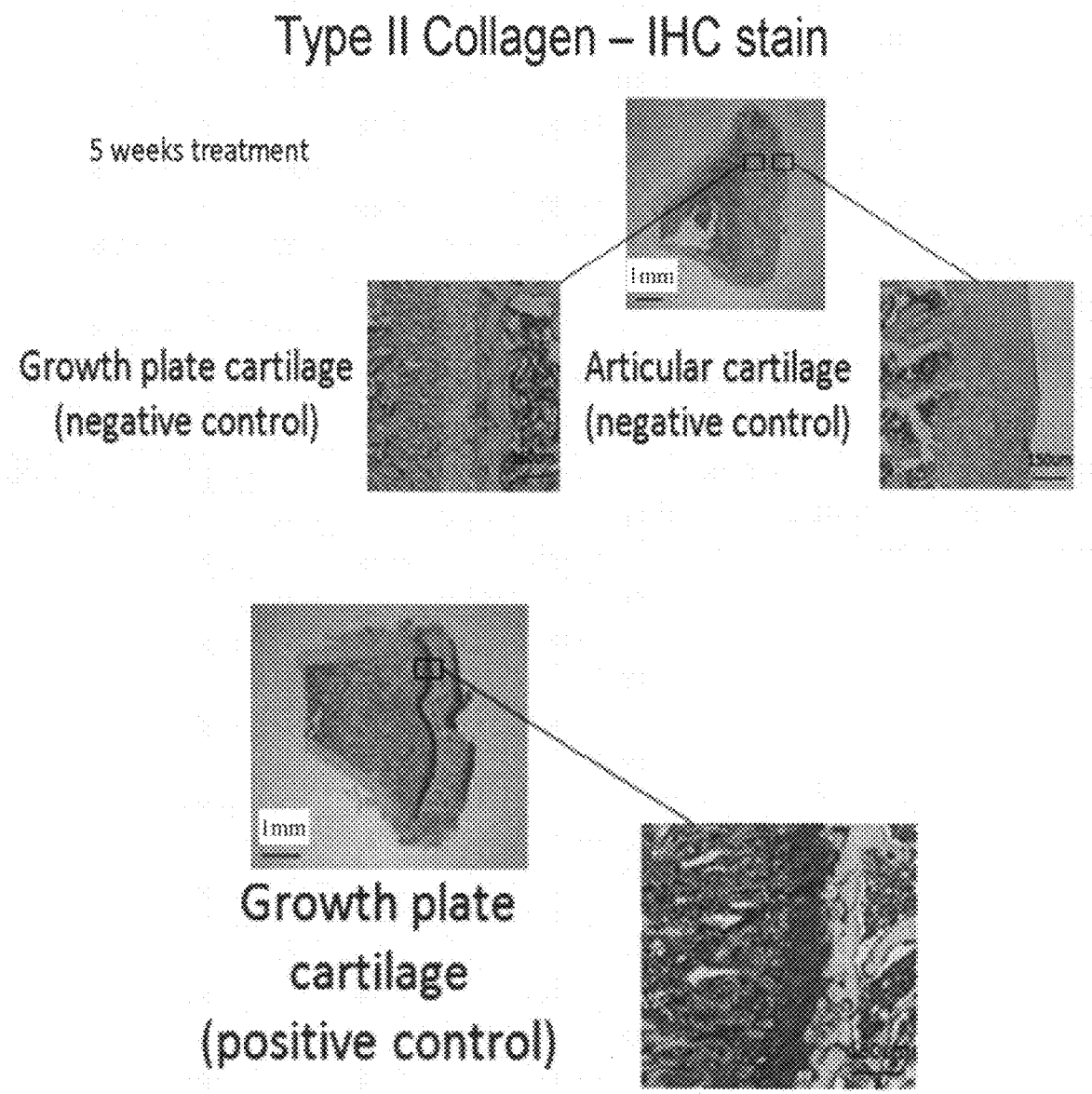

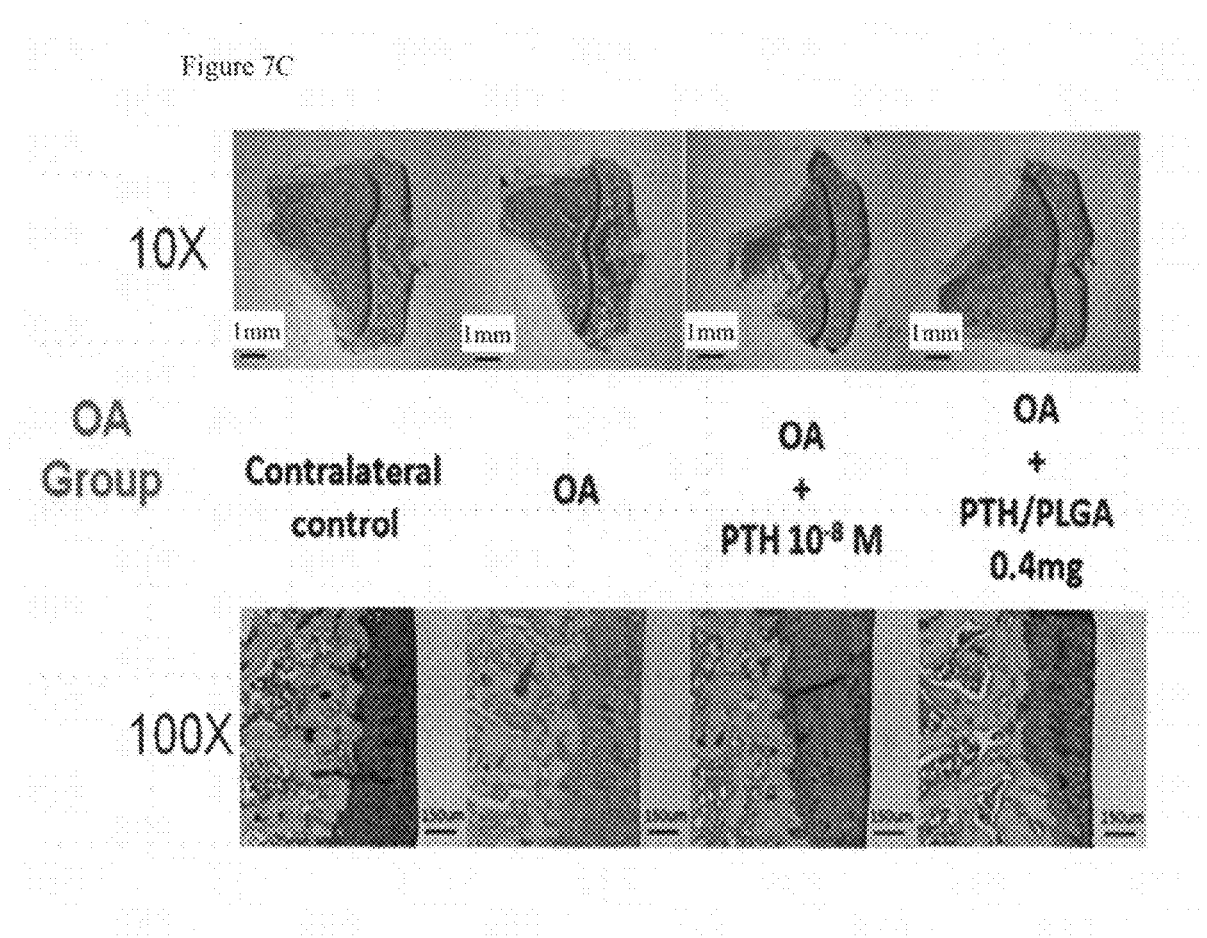

Type X Collagen – IHC stain
5 weeks treatment

Growth plate cartilage
(positive control)
400X

Growth plate cartilage
(negative control)
400X

Articular cartilage
(negative control)
400X

SEQUENCE LISTING

```
<160> NUMBER OF SEQ ID NOS: 2

<210> SEQ ID NO 1
<211> LENGTH: 84
<212> TYPE: PRT
<213> ORGANISM: Homo sapiens
<220> FEATURE:
<221> NAME/KEY: PEPTIDE
<222> LOCATION: (1)..(84)

<400> SEQUENCE: 1

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His Glu
    50                  55                  60

Lys Ser Leu Gly Glu Ala Asp Lys Ala Asn Val Asp Val Leu Thr Lys
65                  70                  75                  80

Ala Lys Ser Gln

<210> SEQ ID NO 2
<211> LENGTH: 34
<212> TYPE: PRT
<213> ORGANISM: Homo sapiens
<220> FEATURE:
<221> NAME/KEY: MISC_FEATURE
<222> LOCATION: (1)..(34)

<400> SEQUENCE: 2
```

-continued

```
Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe
```

METHOD FOR CONTROLLED RELEASE OF PARATHYROID HORMONE FROM ENCAPSULATED POLY(LACTIC-GLYCOLIC)ACID MICROSPHERES

FIELD OF THE INVENTION

The present invention relates to a method for producing a controlled release microsphere for controlled release of a pharmaceutically effective amount of a biologically active polypeptide with activity similar to parathyroid hormone, and a controlled release microsphere prepared by the method and use thereof.

BACKGROUND OF THE INVENTION

Human Parathyroid hormone (PTH) is an 84 amino acids residue polypeptide sequence as shown in SEQ ID NO: 1 (Keutmann. H T, Sauer. M M, Hendy. G N, O'Riordan. J L H, Potts. J T. Complete amino acid sequence of human parathyroid hormone, Biochemistry 17; 1978; 5723), which acts as the most important regulator of calcium homeostasis in the human body through its direct action on bone and kidney. Recent reports and studies in humans with certain analogs of PTH have demonstrated an anabolic effect on bone (Podbesek R, Edouard C, Meunier P J, Parsons J A, Reeve J, Stevenson R W, et al. Effects of two treatment regimes with synthetic human parathyroid hormone fragment on bone formation and the tissue balance of trabecular bone in greyhounds. Endocrinology 1983; 112:1000-6), and have leaded much interest in its use for the treatment of bone disorders.

PTH (1-34), PTH (1-31), and PTH (1-38) exhibits full biological activity of the full-length PTH(1-84) in osteoblasts. In recent years many methods have been investigated for the administration of PTH to the treatment in clinical trials (Neer R M, Arnaud C D, Zanchetta J R, Prince R, Gaich G A, Reginster J-Y, Hodsman A B, Eriksen E F, Ish-Shalom S, Genant H K, Wang O, Mitlak B H. Effect of parathyroid hormone (1-34) on fractures and bone mineral density in postmenopausal women with osteoporosis. Engl J Med 2001; 344:1434-41). A recent reported method emphasized the oral administration of PTH (1-34) showed biologically active. However, the bioavailability of PTH is only 5% and 2.1%, in comparison to subcutaneous administration (Leone-Bay A, Sato M, Paton D, Hunt A H, Sarubbi D, Carozza M, Chou J, McDonough J, Baughman R A. Oral delivery of biologically active parathyroid hormone. Pharm Res 2001; 18(7):964-70). On the other hand, the pulmonary route has shown 40% and 34% bioavailabilities of PTH (1-34) by means of intratracheal instillation or inhalation of dry powders, respectively (Codrons V, Vanderbist R, Verbeeck R K, Arras M, Lison D, Preat V, Vanbever R. Systemic delivery of parathyroid hormone (1-34) using inhalation dry powders in rats. J Pharm Sci 2003; 92(5):938-50). In addition to that for intermittent PTH delivery include programmed administration by osmotic pump and pulsatile transdermal administration (Suzuki Y, Nagase Y, Iga K, Kawase M, Oka M, Yanai S, Matsumoto Y, Nakagawa S, Fukuda T, Adachi H, Higo N, Ogawa Y. Prevention of bone loss in ovariectomized rats by pulsatile transdermal iontophoretic administration of human PYH (1-34). J Pharm Sci 2002; 91:350-61). Both of these methods showed equivalent anabolic actions of PTH on bone like subcutaneous administration. Human PTH (1-38) has also shown similar results. There is relatively little work focusing on local delivery of PTH. Notably, these few studies indicated that PTH administered locally via a direct gene delivery which was found to be beneficial in the treatment of bony defects (Bonadio J, Smiley E, Patil P, Goldstein S. Localized, direct plasmid gene delivery in vivo: prolonged therapy results in reproducible tissue regeneration. Nat Med 1999; 5: 753-9).

PTH (1-34), also called teriparatide, is commercially available in market under the brand name FORTEO® manufactured by Eli Lilly, Indianapolis, Ind., for the treatment of osteoporosis in postmenopausal women with high risk of fracture (Zhang, S, Eli Lilly and company, Indianapolis, Iowa (US). U.S. Pat. No. 6,590,081-B1). This drug is administered by once in daily subcutaneous injection of PTH (1-34) formulations (acetate buffer, mennitol, and m-cresol in water, pH 4). However, many people had adverse response to injections, and thus become non-compliance with the prescribed dosing of the PTH.

Recently, the Applicant found that PTH (1-34) acts on articular chondrocytes to suppress their terminal differentiation, and it can also suppress papain-induced osteoarthritis in rats (Chang. J K, Chang. L H, Hung. S H, Wu. S C, Lee. H Y, Lin. Y S, Chen. C H, Fu. Y C, Wang. G J, Ho. M L, Arthritics and Rheumatology 2009; 60; 3049-3060). But, the treatments requires the administration of drug once in 3 days, which makes more sufferings and inconvenient for patient undergoing treatment. Thus, there is a need to develop a new controlled releasing carrier formulation of a parathyroid hormone peptide in order to reduce the patient suffering and that has suitable bioavailability such that therapeutic level can be achieved for effective treatment of PTH related disorders.

However, in general protein and peptide are unstable in the gastrointestinal tract, have short half-lives, and bio-availability of their aqueous formulations are very low (Fix, J A. Oral controlled release technology for peptides: status and future prospects, Pharm. Res. 1996 December; 13(12):1760-4). These properties make challenge their effective usage in clinical applications.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

(\*\*) p<0.01, comparison between the contralateral and study joints in the sample group at each time point. (##) p<0.01 in comparison with the study joints in the OA groups at each time point.

Figure 7B:
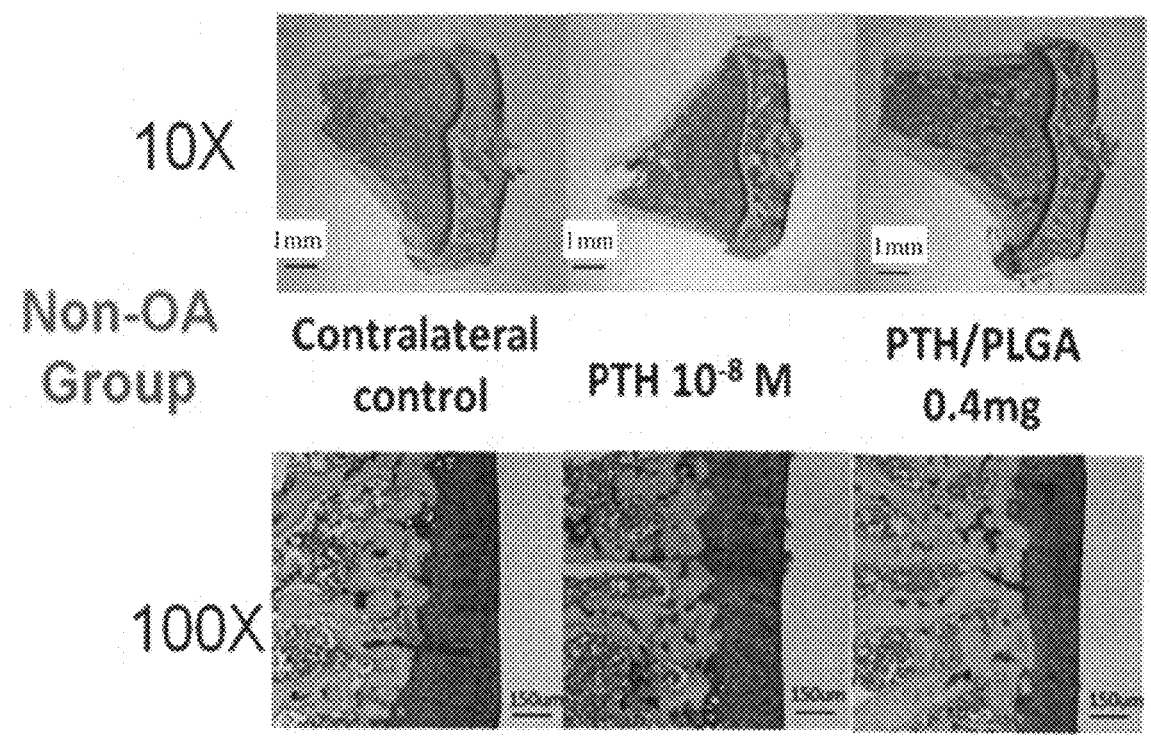

FIG. 7 shows histological analysis of type II collagen (COL. II) stained in contralateral control, Non-OA+PTH, Non-OA+PTH/PLGA, OA, OA+PTH, and OA+PTH/PLGA articular cartilages. Representative the immuno-stained articular cartilages of proximal tibiae from the contralateral joints of rats in the OA, OA+PTH(1-34)($10^{-8}$M) group that treated every 3 days and OA+PTH/PLGA 0.4 mg groups treated 2 times every 15 days in the OA group and the study joints of rats are shown. Growth plate cartilage was stained as the positive control. Growth plate and articular cartilages that was stained without primary anti-body were used as the negative control. COL. II was stained brown. Each bar represents the mean±SEM of eight samples. Data were evaluated by one-way ANOVA and multiple comparisons were performed by Scheffe's method.

(\*\*) p<0.01, comparison between the contralateral and study joints in the sample group at each time point. (##) p<0.01 in comparison with the study joints in the OA groups at each time point.

FIG. 8 shows histological analysis of type X collagen (COL. X) stained in contralateral control, Non-OA+PTH, Non-OA+PTH/PLGA, OA, OA+PTH, and OA+PTH/PLGA articular cartilages. Representative the immuno-stained articular cartilages of proximal tibiae from the contralateral joints of rats in the OA, OA+PTH(1-34) ($10^{-8}$M) group that treated every 3 days and OA+PTH/PLGA 0.4 mg groups treated 2 times every 15 days in the OA group and the study joints of rats are shown. Growth plate cartilage was stained as the positive control. Growth plate and articular cartilages that was stained without primary anti-body were used as the negative control. COL. X was stained brown. COL. X-stained chondrocytes are indicated by arrows.

SUMMARY OF THE INVENTION

The present invention relates to a method for controlled release of parathyroid hormone from encapsulated poly(lactic-glycolic)acid microspheres.

DETAILED DESCRIPTION OF THE INVENTION

Natural and synthetic polymeric carriers (micro- and nanospheres) have been developed as an effective method to control the release of the encapsulated protein and to protect them from degradation (Lu L, Stamatas G N, Mikos A G. Controlled release of transforming growth factor beta1 from biodegradable polymer microparticles. J Biomed Mater Sci 2000; 50:440-51). Among these due to their excellent biocompatibility and biodegradability through natural pathways makes, poly(lactic-co-glycolic acid) (PLGA) and poly(lactic acid) (PLA) were more appropriate for the application of drug delivery. Therefore, the present invention provides a method to fabricate a stable and controlled release of PTH for long durations with therapeutic concentration and bioavailability.

The present invention disclosed a compatible method for fabricating biologically active, stabilized parathyroid hormone (PTH) encapsulated poly(lactic-co-glycolic) acid microspheres for controlled release. The parathyroid hormone (PTH) was successfully encapsulated in two different composition of PLGA. And also the composition was invented for stabilizing the PTH in microspheres through prolonged period of controlled release. The fabricated PLGA microspheres released the biologically active, non-aggregated PTH with effective therapeutic concentration range about $1 \times 10^{-7}$M to $5 \times 10^{-9}$ M for 18 days. The released PTH was verified stable and biological activity over the prolonged period of controlled release.

In the present invention, the stable controlled release of PTH(1-34) encapsulated in PLGA microspheres were fabricated and studied. PTH(1-34) is not stable by changes of pH and temperature. Therefore, the present invention provides a method to stabilize the PTH (1-34) for long time encapsulation.

The present invention illustrates the feasibility of achieving controlled local delivery of PTH(1-34) and maintain their constant concentration by PLGA encapsulation method. Therefore, the PTH(1-34) encapsulated PLGA microsphere may be a potential carrier for PTH(1-34) delivery system, which can constantly deliver the PTH(1-34) for a period of time at effective range of concentration. Accordingly, the PTH(1-34) encapsulated PLGA microspheres can be used to treat the PTH insufficiency disorders, osteoporosis and osteoarthritis etc.

The terms used in the description herein will have their ordinary and common meaning as understood by those skilled in the art, unless specifically defined otherwise. As used throughout the instant application, the following terms shall have the following meanings:

"PTH (1-34)" refers to a 34 amino acids residue polypeptide sequence from the 1$^{st}$ amino acid to the 34$^{th}$ amino acid of SEQ ID NO: 1. For clarity, the polypeptide sequence of PTH (1-34) is shown in SEQ ID NO: 2.

"PTH (1-31)" refers to a 31 amino acids residue polypeptide sequence from the 1$^{st}$ amino acid to the 31$^{th}$ amino acid of SEQ ID NO: 1.

"PTH (1-38)" refers to a 38 amino acids residue polypeptide sequence from the 1$^{st}$ amino acid to the 38$^{th}$ amino acid of SEQ ID NO: 1.

"PTH (1-84)" refers to a full-length Human Parathyroid hormone, of which the polypeptide sequence is shown in SEQ ID NO: 1.

"Degenerative bone disorder" refers to a disease or condition characterized by a decrease in bone mass and/or an increase in probability of fractures because of compromised structural integrity of the bone. Many degenerative bone disorders arise from an imbalance between bone formation and bone resorption. This imbalance can be caused by a reduction in osteoblast mediated bone formation, an increase in osteoclast mediated bone resorption, or a combination of changes to osteoblast and osteoclast activity.

"Osteoporosis" refers to a degenerative bone disorder characterized by low bone mass and microarchitectural deterioration of bone tissue, leading to enhanced bone fragility and increased fracture risk. Primary osteoporosis represents bone mass loss unassociated with any other illness and is typically related to aging and age-related loss of gonadal function. Forms of primary osteoporosis are postemenopausal osteoporosis and senile osteoporosis. Primary osteoporosis also includes idiopathic osteoporosis, which is osteoporosis where an underlying or secondary cause of the bone degeneration is unknown. Secondary osteoporosis refers to osteoporosis resulting from another condition or illness besides the age-related bone degeneration encompassed by primary osteoporosis. The WHO defines osteoporosis as bone density 2.5 standard deviations below the bone density of a reference standard (i.e., generally a healthy young adult of about 30 years old).

"Osteonecrosis" refers to a type of disease that can lead to bone collapse caused by an inadequate supply of blood to the bone tissue. As a living tissue, bone requires a certain amount of blood in order to function properly. Without an adequate blood supply, a serious case of osteonecrosis can develop that leads to the death of bone tissue.

"Osteoarthritis" (OA, also known as degenerative arthritis or degenerative joint disease), refers to a group of diseases and mechanical abnormalities involving degradation of joints, including articular cartilage and the subchondral bone next to it. Clinical manifestations of OA may include joint pain, tenderness, stiffness, creaking, locking of joints, and sometimes local inflammation. In OA, a variety of potential forces—hereditary, developmental, metabolic, and mechanical—may initiate processes leading to loss of cartilage—a strong protein matrix that lubricates and cushions the joints.

Therefore, the present invention provides a controlled release microsphere with mean average size greater than 50 μm, which is produced by preparing a water-in-oil (w/o) emulsion comprising an inner aqueous layer containing a pharmaceutically effective amount of a biologically active polypeptide with activity similar to parathyroid hormone, and an oil layer containing a polymer substance of poly(lactic-co-glycolic acid) (PLGA), then adding the w/o emulsion into aqueous polyvinyl alcohol (PVA) solution to form a water-in-oil-in-water (w/o/w) double emulsion and then desorbing the solvent in the oil layer. In a preferred embodiment, the poly(lactic-co-glycolic acid) (PLGA) is PLGA(50:50) or PLGA (65:35), and the amino acid sequence of the polypeptide consists of SEQ ID NO: 2, which is stabilized in a stock solution comprising hydrochloric acid and bovine serum albumin. Preferably, the concentration of hydrochloric acid is from about 1 mM to about 8 mM, and the concentration of bovine serum albumin is from about 0.01% to about 5%. More preferably, the concentration of hydrochloric acid is from about 2 mM to about 6 mM, and the concentration of bovine serum albumin is from about 0.05% to about 0.15%.

In a preferred embodiment, the polypeptide is released with effective therapeutic concentration range from about $1\times10^{-7}$ M to about $5\times10^{-9}$ M for at least 18 days, the weight percentage of aqueous PVA solution is from about 0.1% to about 5%, and the encapsulation rate of the biologically active polypeptide is not lower than about 60%. Preferably, the weight percentage of aqueous PVA solution is from about 0.5% to about 1.5%.

The present invention further provides a method for producing a controlled release microsphere with mean average size greater than 50 μm, which comprises preparing a water-in-oil (w/o) emulsion comprising an inner aqueous layer containing a pharmaceutically effective amount of a biologically active polypeptide with activity similar to parathyroid hormone, and an oil layer containing a polymer substance of poly(lactic-co-glycolic acid) (PLGA), then gradually adding the w/o emulsion into aqueous polyvinyl alcohol (PVA) solution to form a water-in-oil-in-water (w/o/w) double emulsion and then desorbing the solvent in the oil layer. In a preferred embodiment, the poly(lactic-co-glycolic acid) (PLGA) is PLGA(50:50) or PLGA (65:35), and the amino acid sequence of the polypeptide consists of SEQ ID NO: 2, which is stabilized in a stock solution comprising hydrochloric acid and bovine serum albumin. Preferably, the concentration of hydrochloric acid is from about 1 mM to about 8 mM, and the concentration of bovine serum albumin is from about 0.01% to about 5%. More preferably, the concentration of hydrochloric acid is from about 2 mM to about 6 mM, and the concentration of bovine serum albumin is from about 0.05% to about 0.15%.

In a preferred embodiment, the polypeptide is released with effective therapeutic concentration range from about $1\times10^{-7}$ M to about $5\times10^{-9}$ M for at least 18 days, the weight percentage of aqueous PVA solution is from about 0.1% to about 5%, and the encapsulation rate of the biologically active polypeptide is not lower than about 60%. Preferably, the weight percentage of aqueous PVA solution is from about 0.5% to about 1.5%.

The present invention still further provides a method for providing controlled release delivery of a therapeutic polypeptide to a subject comprising: administering to the subject a controlled release microsphere with mean average size greater than 50 μm, which is produced by preparing a water-in-oil (w/o) emulsion comprising an inner aqueous layer containing a pharmaceutically effective amount of a biologically active polypeptide with activity similar to parathyroid hormone, and an oil layer containing a polymer substance of poly(lactic-co-glycolic acid) (PLGA), then gradually adding the w/o emulsion into aqueous polyvinyl alcohol (PVA) solution to form a water-in-oil-in-water (w/o/w) double emulsion and then desorbing the solvent in the oil layer. In a preferred embodiment, the poly(lactic-co-glycolic acid) (PLGA) is PLGA(50:50) or PLGA (65:35), and the amino acid sequence of the polypeptide consists of SEQ ID NO: 2, which is stabilized in a stock solution comprising hydrochloric acid and bovine serum albumin. Preferably, the concentration of hydrochloric acid is from about 1 mM to about 8 mM, and the concentration of bovine serum albumin is from about 0.01% to about 5%. More preferably, the concentration of hydrochloric acid is from about 2 mM to about 6 mM, and the concentration of bovine serum albumin is from about 0.05% to about 0.15%.

In a preferred embodiment, the polypeptide is released with effective therapeutic concentration range from about $1\times10^{-7}$ M to about $5\times10^{-9}$ M for at least 18 days, and the weight percentage of aqueous PVA solution is from about 0.1% to about 5%. Preferably, the weight percentage of aqueous PVA solution is from about 0.5% to about 1.5%.

In a preferred embodiment, the subject is suffered from a PTH insufficiency disorder, bone disorder or cartilage disorder. In a more preferred embodiment, the bone disorder is osteoporosis or osteonecrosis; the cartilage disorder is osteoarthritis. In another more preferred embodiment, the subject is human.

EXAMPLES

The examples below are non-limiting and are merely representative of various aspects and features of the present invention.

Example 1

Microsphere Preparation and Characterization

Figure 1:
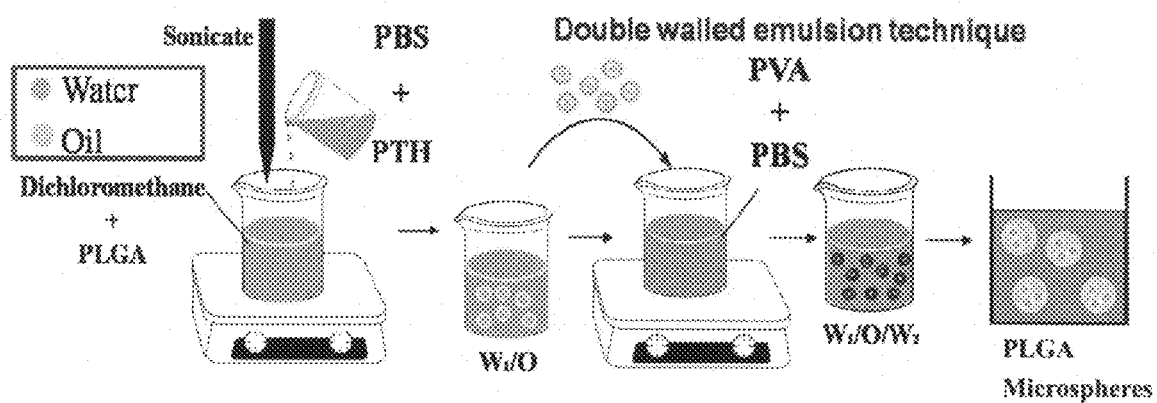
FIG. 1 shows fabrication of PTH(1-34) encapsulated PLGA microspheres.

Two different composition of PLGA, PLGA(50:50) and PLGA (65:35) were used in this study. The microspheres were fabricated by the w/o/w double emulsion technique (FIG. 1). Briefly, 90 ul of PTH (1-34) stock solution (PTH in 4 mM HCl/0.1% bovine serum albumin (BSA) solution) was emulsified in a 10% polymer solution in dichloromethane (DCM), using a probe sonicator at an output power of 15 W (Virsonic 100, Cardiner, N.Y.) for 20 sec over an ice bath to form primary water-in-oil (w/o) emulsion. The water-in-oil-in-water (w/o/w) double emulsion was formed by gradual addition of the w/o emulsion into the 20 ml of 1% aqueous polyvinyl alcohol (PVA) solution under vigorous stirring. The solution was stirred at room temperature for 30 mins to harden the microspheres, followed by the dichloromethane was evaporated under water suction and then centrifuged to collect solid microspheres. The resultant microspheres were washed with distilled water three times and freeze dried. The overall morphology of the microspheres was examined using scanning electron microscopy (SEM) (Hitachi 53200, Tokyo, Japan) after gold coating of the microsphere samples on a stub and the mean size of the microspheres were measured by particle size analyzer.

Figure 2:
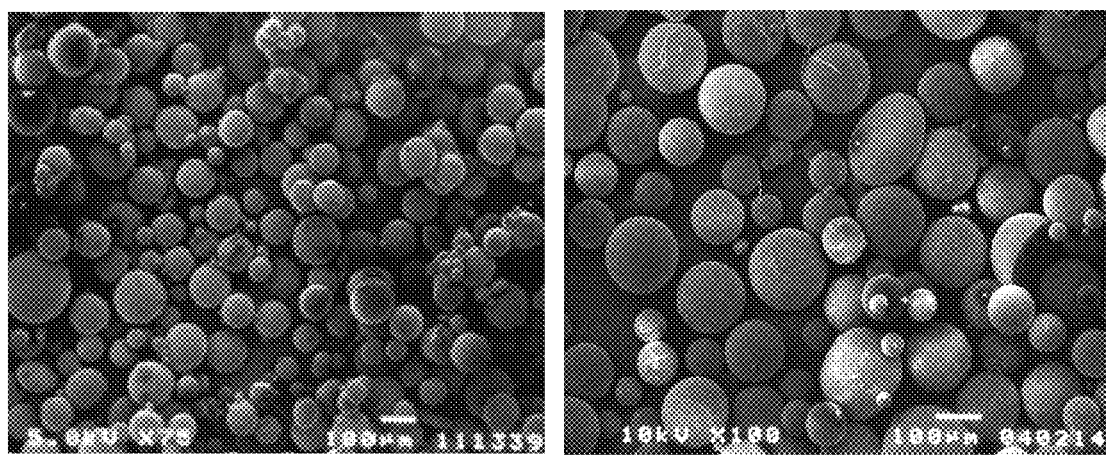
FIG. 2 shows SEM images of PTH(1-34) encapsulated PLGA microspheres.
Figure 3A:
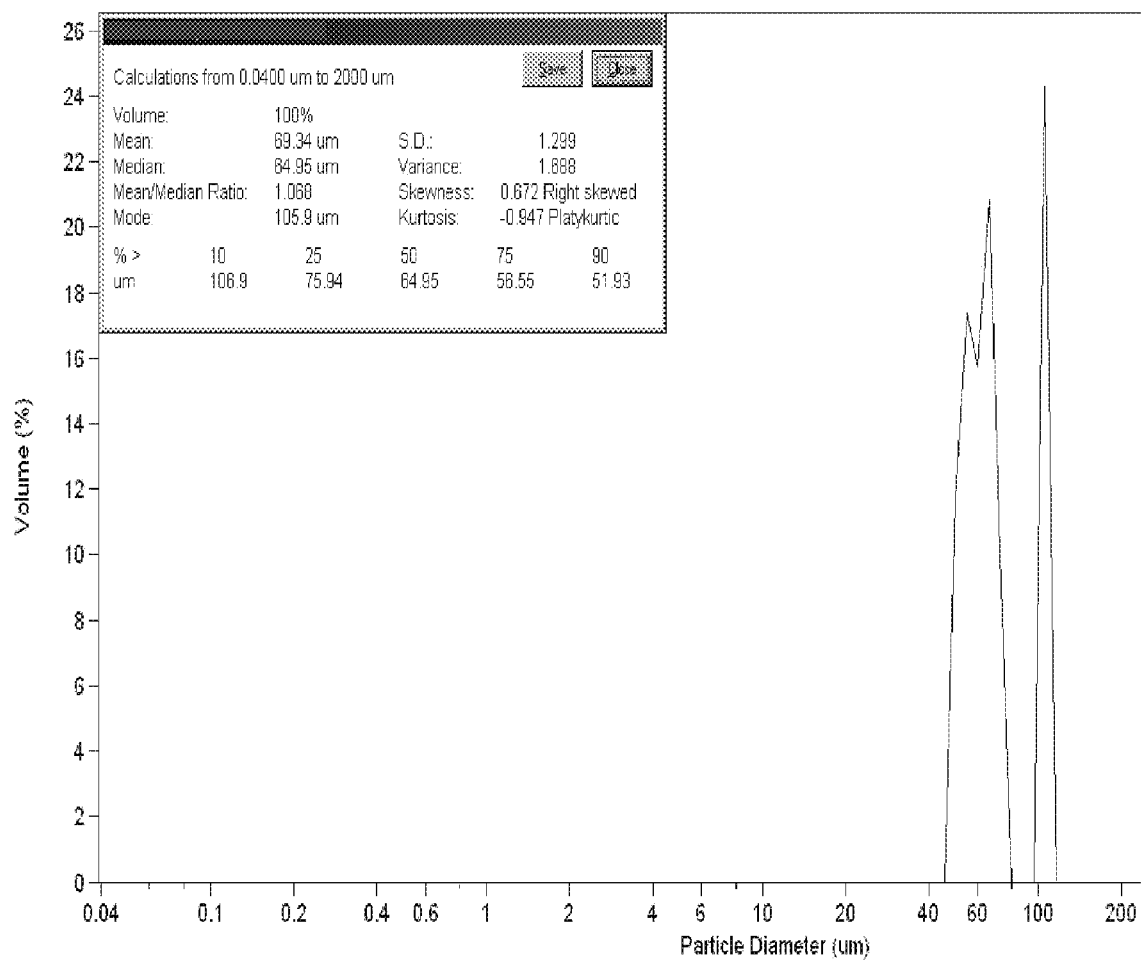
FIG. 3 shows (a) Size of the microspheres by particle size analyzer and (b) Cytotoxicity of PTH(1-34) by MTT analysis.

4 mM Hydrochloric acid and normal saline (0.9% NaCl) and 0.1% BSA were used as the stabilizers to protect the PTH(1-34) in encapsulated microspheres. For controlled release of drugs from encapsulated microspheres the surface of the microspheres should be smooth. The SEM observation emphasized that the surface of the PLGA microspheres were smooth and consistent through the degradation. The literature reports emphasized that the appropriate size of the microsphere for intra-articular injection in rat is 35-105 μm (Butoescu. N, Jordan. 0, Doelker. E, Intra-articular drug delivery systems for the treatment of rheumatic diseases: A review of the factors influencing their performance European Journal of Pharmaceutics and Biopharmaceutics, 2009; 73; 205-218). The particle analyzer data showed that using the method of the present invention successfully fabricated >90% microspheres with narrow mean average size of 45-80 μm (FIGS. 2 and 3a).

Example 2

Encapsulation and Release Kinetics

Ten-milligram PTH(1-34)-loaded microspheres were suspended in a mixture of 1 mL of 0.9% NaCl and 200 uL of dichloromethane with vigorous shaking at room temperature for 1 h. PTH(1-34) standard solutions (0.1 ml) were also prepared by adding 0.9% NaCl and 0.1% BSA. Concentration of PTH(1-34) was measured using a commercially available immunoassay kit following the manufacturer's instructions. Protein loading and encapsulation efficiency were determined by Eqs. (1) and (2), respectively (Table 1).

Protein loading (w/w%)=Amount of protein in microspheres/Amount of microspheres   Eqs. (1)

Encapsulation efficiency (%)=(Measured protein Conc./Theoretical protein conc.)×100   (2)

TABLE 1

Encapsulation efficiency of PTH(1-34) in PLGA microspheres

| PLGA | Theoretical conc. of PTH(ng/mL) | Measured conc. of PTH (ng/mL). | Encapsulation Rate |
|---|---|---|---|
| 50:50 | 1800 | 1319.0 | 73.3% |
| 65:35 | 1800 | 1129.4 | 62.7% |

Example 3

In Vitro PTH(1-34) Release

In vitro PTH(1-34) release profiles from PLGA microspheres were determined as follows. Ten milligrams microspheres were suspended in 1 ml PBS (pH=7.4). The microsphere suspensions were incubated at 4, 25 and 37° C. without shaking. At designated time interval 1 ml release medium was collected by centrifugation and replaced with equal amount of fresh PBS. The concentration of PTH(1-34) in the release medium was measured by using a PTH(1-34) ELISA kit with PTH antibody coated wells using the manufacturer's recommendations (Immutopics, San Clemente, Calif.). Triplicate wells were used for each time point. Absorbance measurements read at 450 nm recorded by a microtiter plate reader were used to calculate the PTH concentrations by the log-logit method using the GraphPad Prisms program (GraphPad Software, San Diego, Calif.) with a standard curve.

Figure 4:
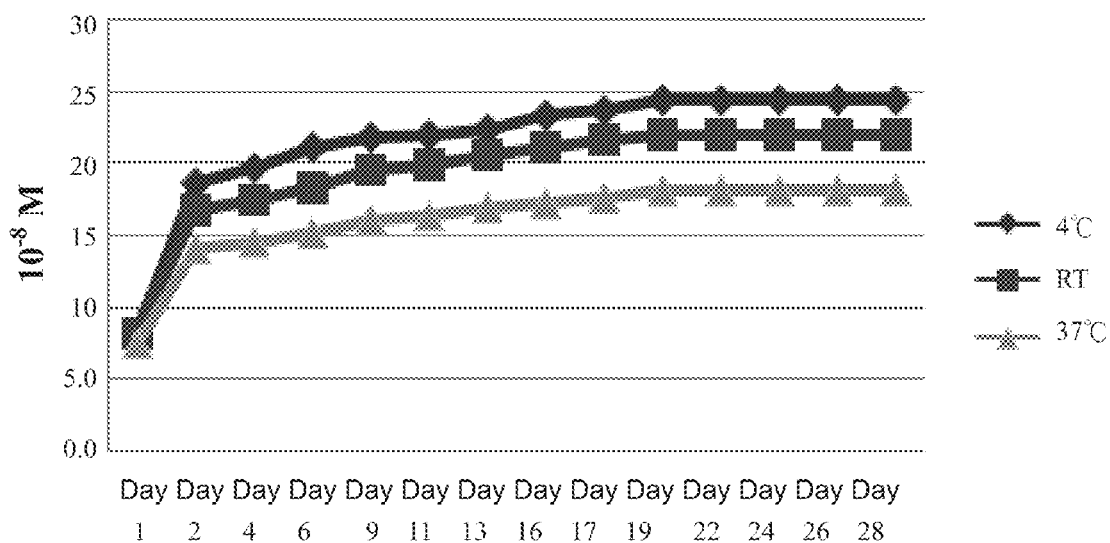
FIG. 4 shows cumulative release profile of PLGA (50:50) and PLGA(65:35).
Figure 4:
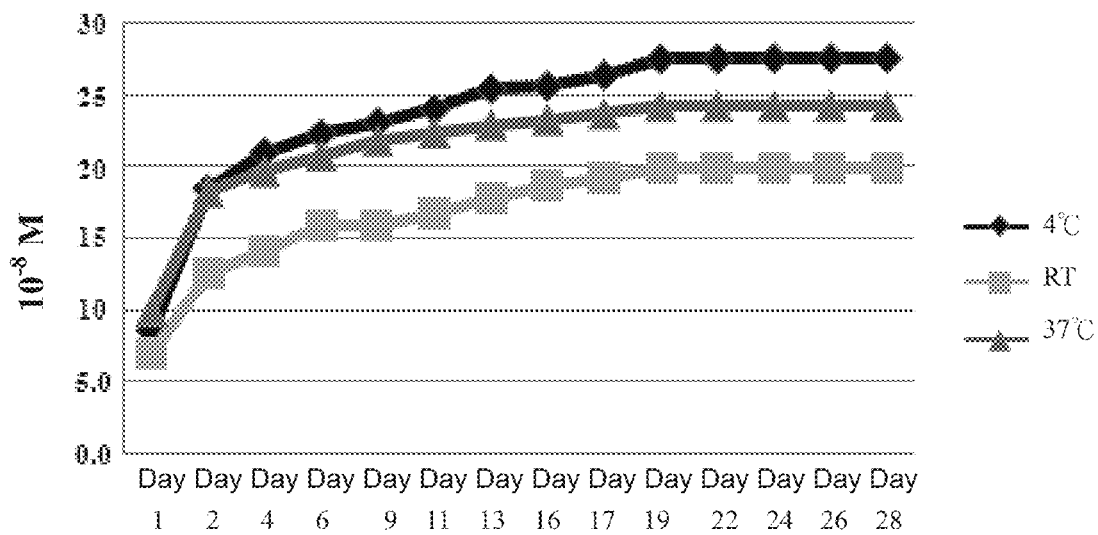

A recent report from the Inventors suggested that the effective dose of PTH (1-34) for the treatment of papain induced osteoarthritis in a rat was $10^{-8}$ M and the injection rate was once in three days for 5 weeks. The release kinetic data from PTH (1-34) specific ELISA analysis showed that PLGA(65:35) microspheres released the PTH(1-34) for 2 weeks with desired concentration range of $10^{-7}$-$10^{-8}$ M (FIG. 4) at 37° C. In comparison with PLGA (50:50), the PLGA(65:35) showed the consistent release profile over 17 days under mimicking physiological condition in PBS at 37° C.

Example 4

The 3-(4,5-dimethylthiazol-2-yl)-2,5-diphenyltetrazolium bromide (MTT) assay

Figure 3B:
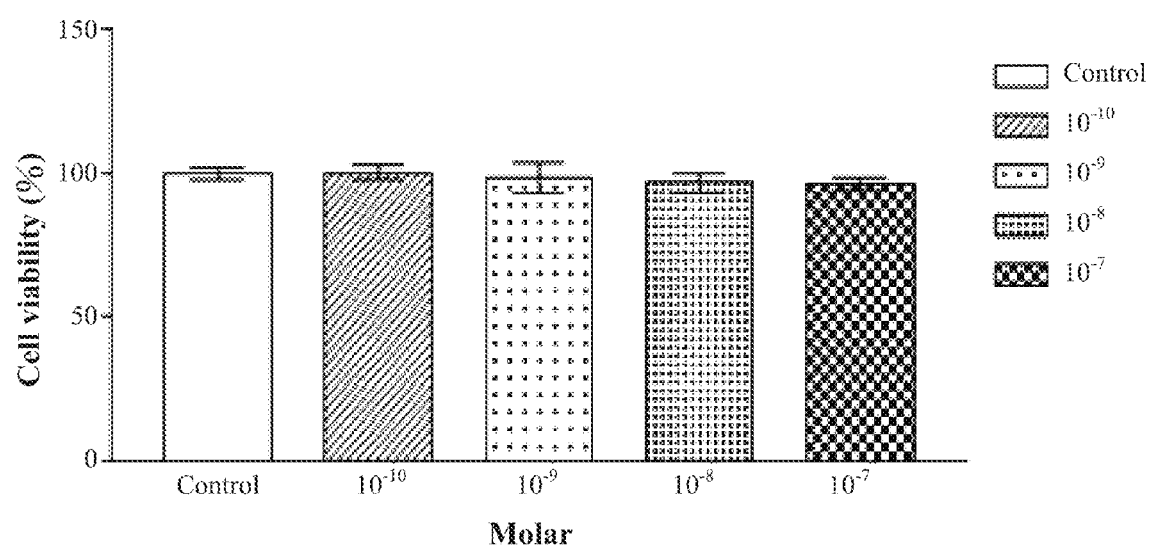

The toxicity range of PTH(1-34) was tested by MTT analysis on treated with MC3T3-E1 (osteoblastic cells). Briefly, the mitochondria activities of the MC3T3-E1 cultured on wells were detected by the conversion of 3-(4,5-dimethylthiazol-2-yl)-2,5-diphenyltetrazolium bromide (MTT) to formazan as previously described, and the quantity of formazan product released into the medium, which is directly proportional to the number of living cells in culture, can be measured by absorbance at 490 nm. At the indicated time interval, freshly prepared MTT reaction mixture diluted in standard medium at 1:5 (MTT:medium) volume ratio were added to the wells containing the cells and then incubated at 37° C. under 5% $CO_2$ for an additional 4 hrs. After the additional incubation, 100 ul of the converted MTT released into medium from each well was transferred to 96-well plates and the absorbance at 490 nm was recorded with a microplate reader (PathTech) using KC junior software (FIG. 3b).

Example 5

Bioactivity of Released PTH(1-34)

Figure 5:
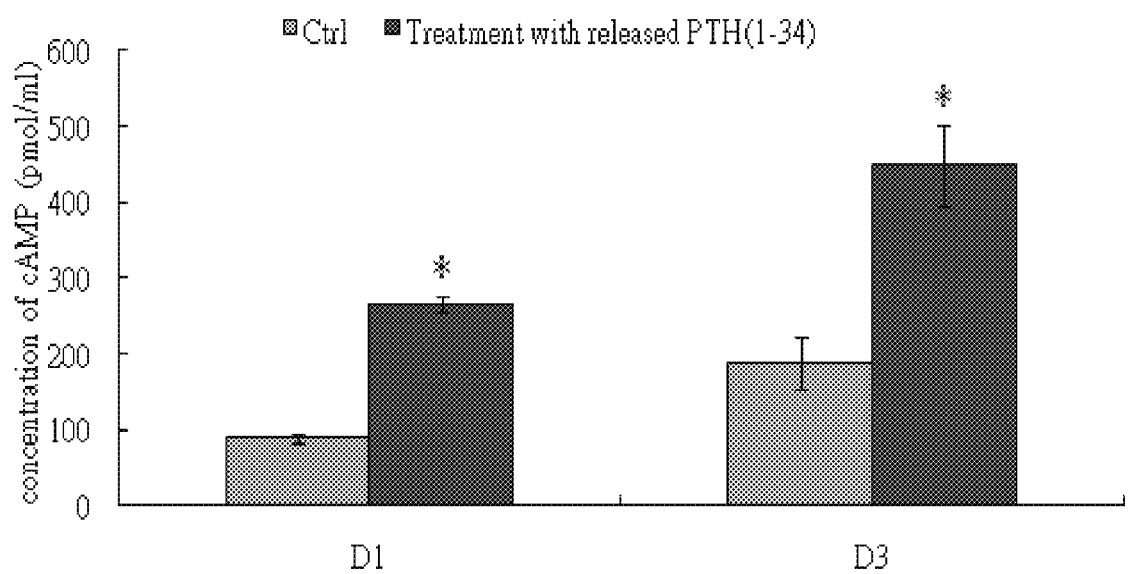
FIG. 5 shows bioactivity of PTH(1-34) from PLGA microsphere on MC3T3-E1 cells.

Activity of controlled released PTH(1-34) was determined by measuring cAMP contents in cells treated with released PTH(1-34). For these experiments, the MC3T3-E1 was cultured in α-MEM supplemented with 10% fetal bovine serum and 50 mg/mL ascorbic acid. The cells were seeded onto 24-well plates at a density of 50,000 cells/well. After 6 hrs of incubation with released PTH (1-34) from microspheres, the cells were lysed directly in the medium by adding 0.1 N HCl and 0.5 mM isobutylmethylxanthine to protect the produced cAMP. Intracellular cAMP was measured using a commercially available ELISA kit (Endogen/Pierce, Rockford, Ill.) following the manufacturer's instructions. The bioactivity data showed that the increased production of cAMP in the released PTH(1-34) treated MC3T3-E1 cells at 1 and 3 days, indicating the released PTH(1-34) possessed bioactivity (FIG. 5).

Example 6

Statistical Analysis

Three independent cultures for biochemical analysis were tested. Each experiment was repeated at least three times, and data (expressed as mean±SEM) from a representative experiment are shown. Statistical significance was evaluated by one-way analysis of variance (ANOVA), and multiple comparisons were performed by Scheffe's method. A $p<0.05$ was considered significant.

Example 7

In Vivo Study

Methods:
Animal Experiments

The animal experiments were approved by the Animal Care and Use Committee of Kaohsiung Medical University. Fifty-four 12-week-old male Sprague-Dawley rats (250-300 gm) were purchased from BioLASCO Taiwan and housed under standard laboratory conditions (temperature 24° C., 12-hour light-dark cycle) with food and water ad libitum. The animals were acclimatized to the laboratory environment for 1 week before the experiments.
Osteoarthritis Induction and PTH Treatment Each left knee, which served as the contralateral control joint, received the vehicle without PTH treatment or OA-induction. The right knees were the study joints. Rats were divided into five groups: Non-OA+PTH [PTH(1-34) treatment without OA-induction] (n=6), Non-OA+PTH/PLGA [PTH/PLGA microspheres treatment without OA-induction] (n=6), OA [OA-induction without PTH(1-34) treatment] (n=6), OA+PTH [PTH(1-34) treatment followed by OA-induction] (n=6), and OA+PTH/PLGA [PTH/PLGA microspheres treatment followed by OA-induction] (n=6). OA was induced in the right knees of rats in the OA and OA+PTH groups with intra-articular injections of 20 µl of 4% papain solution and 20 µl of 0.03 M cystein. The injections were given with a 26-gauge needle via the patellar tendon on days 1, 4, and 7 of the experiment (13). In the OA+PTH group, after OA-induction, the right knees were injected intra-articularly with 40 µl of 10 nM PTH(1-34) every three days until sacrifice. In the PTH group, the same PTH(1-34) treatment was performed but without OA-induction. In the OA+PTH/PLGA group, after OA-induction, the right knees were injected intra-articularly with 0.4 mg of PTH/PLGA microspheres at 1st and 15th day. The rats were sacrificed with an overdose of $CO_2$-inhaled at the same time point at 5 weeks.
Histology After sacrifice, the knees of each rat were harvested, and the tibia plateaus with articular cartilage were collected and fixed with 10% neutral buffered formalin prior to histological preparation. The samples were then decalcified in 10% formic acid/PBS. The decalcified tibia articular samples were paraffin embedded, and 5 µm microsections in the coronary plane were prepared. GAG was stained with Safranin-O-Fast-Green (1% Safranin-O counter-stained with 0.75% hematoxylin and then 1% fast green) (Sigma, St. Louis, Mo.). Localized type II Collagen and type X collagen were immuno-stained.
Histomorphometric Study GAG was stained red by Safarinin-O, and the total and red-stained areas in the articular cartilage of each proximal tibia were measured using the Image-Pro plus 5.0 software (FIG. 6C) (Media Cybernetics Inc. MD, USA). The ratio of red stained area to total area (red/total) in each group was calculated.
Immunohistochemistry The tibia articular sections were re-hydrated, and the endogenous peroxidase in tissues was blocked with 3% hydrogen peroxide. Samples were digested by enzymes for epitope retrieval before incubation with primary antibodies.

Figure 6A:
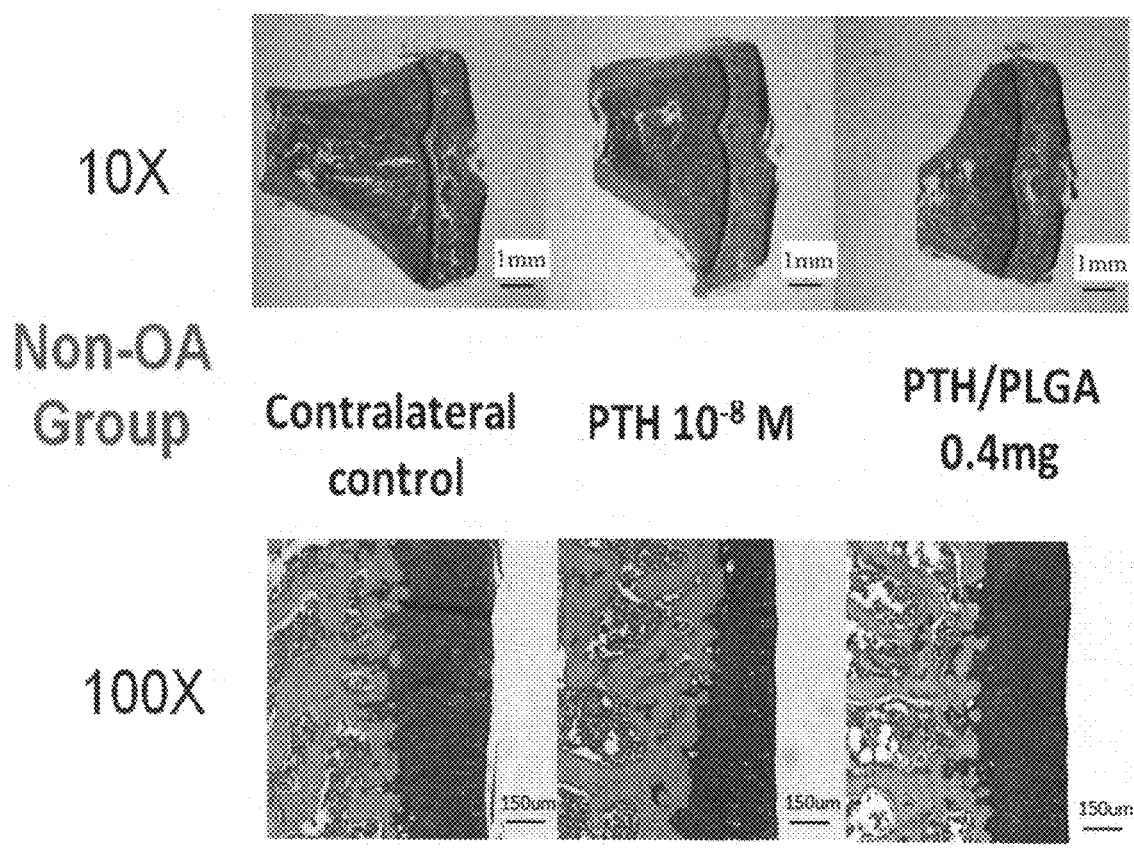
FIG. 6 shows histological analysis of GAG level by Safranin-O-stain in contralateral control, Non-OA+PTH, Non-OA+PTH/PLGA, OA, OA+PTH, and OA+PTH/PLGA articular cartilages. Representative the Safranin-O stained articular cartilages of proximal tibiae from the contralateral joints of rats in the OA, OA+PTH(1-34)($10^{-8}$M) group that treated every 3 days and OA+PTH/PLGA 0.4 mg groups treated 2 times every 15 days in the OA group and the study joints of rats are shown. Each bar represents the mean±SEM of eight samples. Data were evaluated by one-way ANOVA and multiple comparisons were performed by Scheffe's method.
Figure 6B:
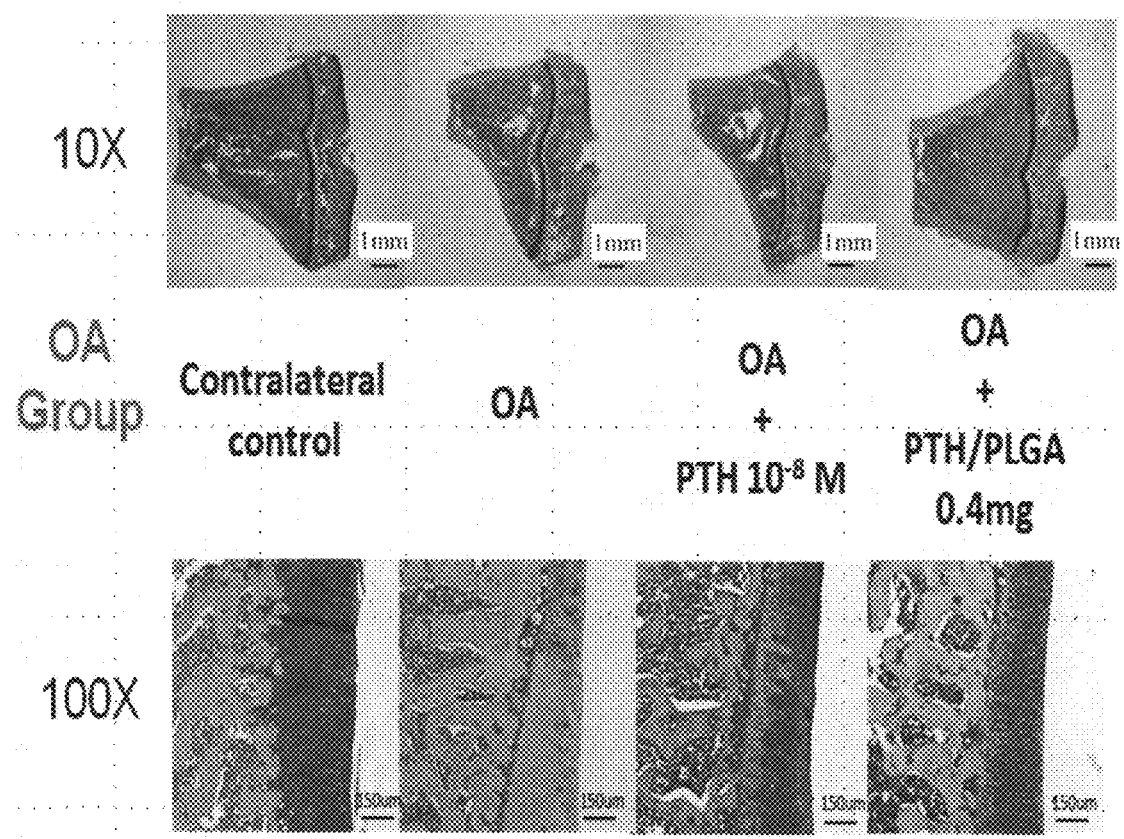

The method for enzyme digestion was modified from a previous report (20). The optimal condition for the enzyme digestion for type II collagen immuno-staining was a mixture of 2.5% hyluronidase and 1 mg/ml pronase in PBS (pH 7.4) (Sigma, St. Louis, Mo.) at 37° C. for 1 hour. For type X collagen immuno-staining the optimal condition was 0.1 U/ml chondroitinase ABC (Sigma, St. Louis, Mo.) for 1 hour and pepsin 1 mg/ml in tris-HCl (pH 3.0) at 37° C. for 15 minutes. Sections were then blocked with fetal bovine serum for 1 hour and incubated with primary antibodies to type II collagen (mouse monoclonal antibody) (Chemicon International, Temecula, Calif.) and type X collagen (rat polyclonal antibody) (1:200) (COSMO, Tokyo, Japan) at $37^2C$ for 4 hour. The 2 antibodies were incubated for 30 minutes using the biotin-labeled goat anti-mouse immunoglobulin for type II collagen (DAKO, Carpinteria, Calif.) and biotin-labeled goat anti-rabbit immunoglobulin for type X collagen (Biocare medical, Walnut Creek, Calif.), and the Streptravidin-HRP (streptavidin conjugated to horseradish peroxidase, Biocare medical, Walnut Creek, Calif.). Staining with a 3,3'-diaminobenzidine solution containing 0.01% hydrogen peroxide resulted in a brown color. Finally, sections were counterstained with hematoxylin and observed on a microscope. The relative density of immuno-staining (density/area; area, 25.44±2.77 $mm^2$) was measured using the Image-Pro plus 5.0 software (FIG. 7C) (Media Cybernetics Inc. MD, USA).
Results:
Histologic and Histomorphometric Studies in Rat Articular Cartilage Sections Representative photomicrographs of Safranin O-stained articular cartilage from the joints of rats in the contralateral control, Non-OA+PTH, Non-OA+PTH/PLGA, OA, OA+PTH, and OA+PTH/PLGA were shown in FIGS. 6 (A&B). The ratio of Safranin O-stained area to total area (red:total) was measured and compared among groups (FIG. 6 C). The red:total ratio in the contralateral control joints was not significant different among every group. The red:total ratio in the cartilage in the contralateral control joint, and the study joints of Non-OA+PTH, and Non-OA+PTH/PLGA groups were also not significantly different (FIG. 6 C). The red:total ratio in the cartilage from the study joint in the OA group was significantly lower than that of the contralateral control cartilages 5 weeks after OA induction (P <0.01) (FIG. 6C). After 5 weeks of PTH(1-34) treatment, cartilage from the OA+PTH group was not significantly different from the contralateral control cartilage (FIG. 6 C). The red:total ratio in the OA+PTH/PLGA group was significantly higher than that in the OA group after 5 weeks (P<0.01) (FIG. 6 C). Other than that the red:total ratio in the OA+PTH/PLGA group was also not significantly different from the contralateral control cartilage. There were no significant differences among OA+PTH, OA+PTH/PLGA and contralateral control cartilages of each group at 5 weeks (FIG. 6 C).
Immunohistochemistry Studies on Type II Collagen in Rat Articular Cartilage Sections Representative photomicrographs of type II collagen-stained (stained brown) articular cartilage from the joints of rats in the contralateral control, Non-OA+PTH, Non-OA+PTH/PLGA, OA, OA+PTH, and OA+PTH/PLGA were shown in FIGS. 7 (A, B, and C). The ratio of type II collagen stained area to total area (brown:total) was measured and compared among groups (FIG. 7 D). The brown:total ratio in the contralateral control joints was not significant different among every group. The red:total ratio in the cartilage in the contralateral control joint, and the study joints of Non-OA+PTH, and Non-OA+PTH/PLGA groups were also not significantly different (FIG. 7 D). The red:total ratio in the cartilage from the study joint in the OA group was significantly lower than that of the contralateral control cartilages 5 weeks after OA induction (P<0.01) (FIG. 7 D). After 5 weeks of PTH(1-34) treatment, cartilage from the OA+PTH group was not significantly different from the contralateral control cartilage (FIG. 7 D). The brown:total ratio in the OA+PTH/PLGA group was significantly higher than that in the OA group after 5 weeks (P<0.01) (FIG. 7 D). Other than that the red:total ratio in the OA+PTH/PLGA group was also not significantly different from the contralateral control cartilage. There were no significant differences among OA+PTH, OA+PTH/PLGA and contralateral control cartilages of each group at 5 weeks (FIG. 7 D).

Figure 8A:
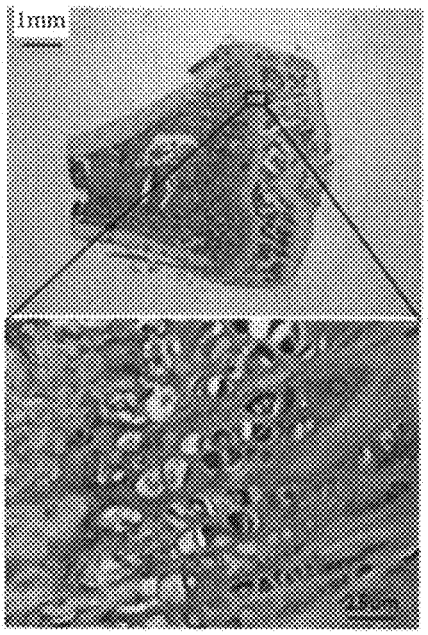
Figure 8A:
Figure 8A:
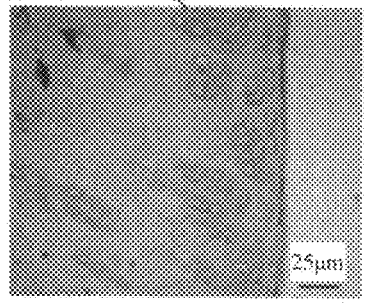
Figure 8B:
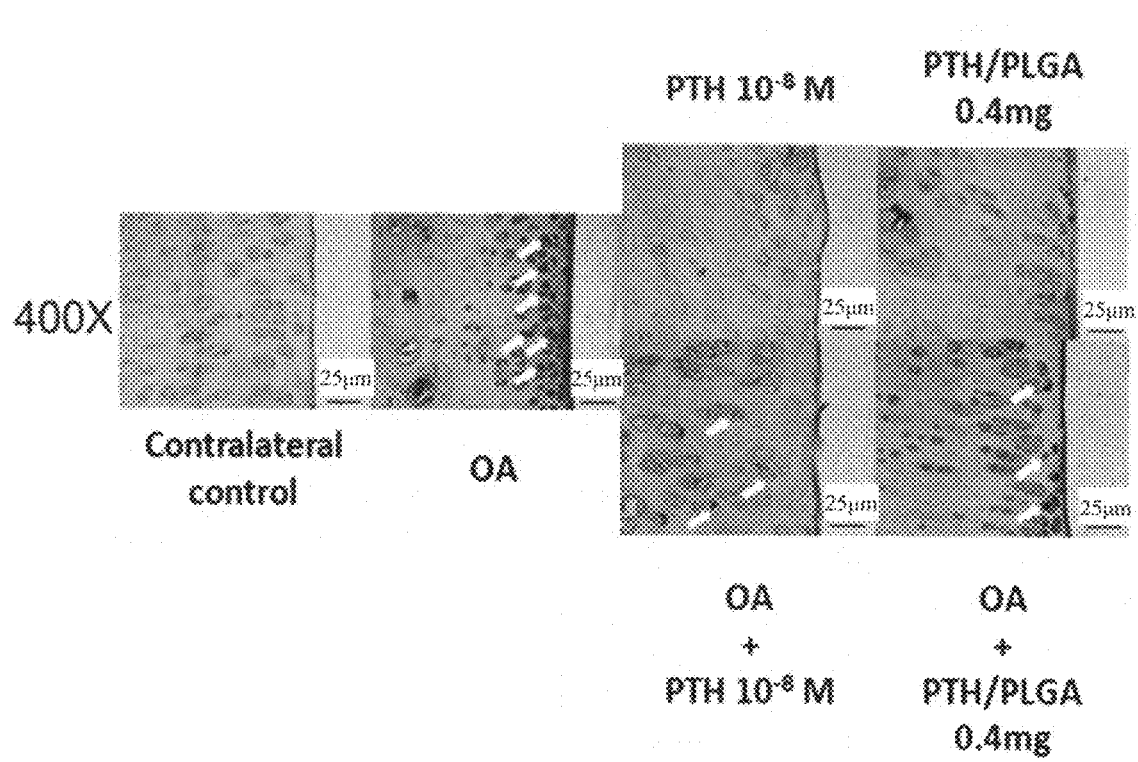

Immunohistochemistry Studies on Type X Collagen in Rat Articular Cartilage Sections No obvious type X collagen-stained chondrocytes were found in the contralateral control cartilage (FIGS. 8A and 8B). Immunolocalized type X collagen (stained brown) was predominantly found in articular chondrocytes from the OA group, but less positive stained cells were found in cartilage in the OA+PTH, and OA+PTH/PLGA groups after 5 weeks of treatment (FIGS. 8A and 8B).

One skilled in the art readily appreciates that the present invention is well adapted to carry out the objects and obtain the ends and advantages mentioned, as well as those inherent therein. The microspheres, and processes and methods for producing them are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations, which are not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

---

What is claimed is:

1. A method for controlled release delivery of biologically active polypeptide with activity similar to parathyroid hormone to a subject suffering from osteoarthritis in effective therapeutic concentration comprising: administrating to the subject a controlled release microsphere with mean average size greater than 50 μm, which is produced by preparing a water-in-oil (w/o) emulsion comprising an inner aqueous layer containing the biologically active polypeptide, and an oil layer containing a polymer substance of poly(lactic-co-glycolic acid) (PLGA), then gradually adding the w/o emulsion into aqueous polyvinyl alcohol (PVA) solution to form a water-in-oil-in-water (w/o/w) double emulsion and then desorbing the solvent in the oil layer, whereby the polypeptide is released in the effective therapeutic concentration ranging from about $1\times10^{-7}$ M to about $5\times10^{-9}$ M for at least 18 days.

2. The method of claim 1, wherein the biologically active polypeptide with activity similar to parathyroid hormone is SEQ ID NO: 2.

3. The method of claim 1, wherein the poly(lactic-co-glycolic acid) (PLGA) is PLGA(50:50) or PLGA (65:35).

4. The method of claim 1, wherein the polypeptide is stabilized in a stock solution comprising hydrochloric acid and bovine serum albumin.

5. The method of claim 4, wherein concentration of the hydrochloric acid is from about 1 mM to about 8 mM, concentration of the bovine serum albumin is from about 0.01% to about 5%.

6. The method of claim 1, wherein weight percentage of the aqueous PVA solution is from about 0.1% to about 5%.

7. The method of claim 1, wherein encapsulation rate of the biologically active polypeptide is not lower than about 60%.

8. The method of claim 1, wherein the subject is human.

* * * * *